(12) United States Patent
Woehr

(10) Patent No.: US 9,623,210 B2
(45) Date of Patent: Apr. 18, 2017

(54) CATHETER ASSEMBLIES WITH WIPEABLE BLOODSTOP AND RELATED METHODS

(71) Applicant: B. BRAUN MELSUNGEN AG, Melsungen (DE)

(72) Inventor: Kevin Woehr, Felsberg (DE)

(73) Assignee: B. Braun Melsungen AG, Melsungen (DE)

( * ) Notice: Subject to any disclaimer, the term of this patent is extended or adjusted under 35 U.S.C. 154(b) by 136 days.

(21) Appl. No.: 13/951,168

(22) Filed: Jul. 25, 2013

(65) Prior Publication Data

US 2014/0276453 A1    Sep. 18, 2014

Related U.S. Application Data

(60) Provisional application No. 61/788,169, filed on Mar. 15, 2013.

(51) Int. Cl.
*A61M 25/06* (2006.01)
*A61M 25/00* (2006.01)
(Continued)

(52) U.S. Cl.
CPC ...... *A61M 25/0618* (2013.01); *A61M 5/3273* (2013.01); *A61M 25/0606* (2013.01);
(Continued)

(58) Field of Classification Search
CPC .......... A61M 25/0618; A61M 25/0015; A61M 25/065; A61M 25/0631; A61M 5/3273;
(Continued)

(56) References Cited

U.S. PATENT DOCUMENTS 3,585,996 A * 6/1971 Reynolds ........... A61M 25/0111
604/158
4,917,668 A * 4/1990 Haindl .................. A61M 39/26
604/167.03
(Continued)

FOREIGN PATENT DOCUMENTS

DE        4434569 A1      3/1995
EP        1785159 A1      5/2007
WO    WO 2011038931 A1 *  4/2011

OTHER PUBLICATIONS

International Search Report for corresponding PCT Application No. PCT/EP2014/055086 filed Mar. 14, 2014, from International Searching Authority (EP) dated May 30, 2014 (4 pages).
(Continued)

*Primary Examiner* — Bhisma Mehta
*Assistant Examiner* — William Frehe
(74) *Attorney, Agent, or Firm* — Klein, O'Neill & Singh, LLP

(57) ABSTRACT

Catheter assemblies are described having a catheter hub with a catheter tube and a needle hub with a needle projecting through the catheter tube. The catheter hub has a valve or a septum for stopping or slowing down the flow of fluid in or out of the catheter hub when the valve or septum is closed. The valve or septum has an exposed proximal wall that enables the valve to be wiped or cleaned with an antiseptic solution. The valve further has a cavity for receiving at least part of a needle guard, which is incorporated for preventing accidental needle stick with the needle tip.

28 Claims, 9 Drawing Sheets

(51) Int. Cl.
*A61M 5/32* (2006.01)
*A61M 39/16* (2006.01)
*A61M 39/06* (2006.01)

(52) U.S. Cl.
CPC ............ *A61M 39/06* (2013.01); *A61M 39/16* (2013.01); *A61M 25/0097* (2013.01); *A61M 39/0693* (2013.01); *A61M 2039/066* (2013.01); *Y10T 29/49826* (2015.01)

(58) Field of Classification Search
CPC ........ A61M 2005/325; A61M 25/0612; A61M 25/0625; A61M 5/1626; A61M 5/3202; A61M 5/3205; A61M 5/321; A61M 39/0693; A61M 25/0097; A61M 25/0693
See application file for complete search history.

(56) References Cited

U.S. PATENT DOCUMENTS

| | | | | |
|---|---|---|---|---|
| 4,935,010 A | * | 6/1990 | Cox | ................... A61M 39/045 604/122 |
| 6,171,287 B1 | | 1/2001 | Lynn et al. | |
| 6,616,630 B1 | * | 9/2003 | Woehr | ................ A61M 5/3273 604/110 |
| 6,908,459 B2 | | 6/2005 | Harding et al. | |
| 7,470,261 B2 | | 12/2008 | Lynn | |
| 2004/0006330 A1 | * | 1/2004 | Fangrow, Jr. | ......... A61M 39/02 604/533 |
| 2006/0155245 A1 | * | 7/2006 | Woehr | ............. A61M 25/0618 604/164.08 |
| 2007/0112305 A1 | * | 5/2007 | Brimhall | .......... A61M 25/0606 604/164.08 |
| 2008/0108944 A1 | * | 5/2008 | Woehr | ................. A61B 5/1411 604/164.08 |
| 2008/0249478 A1 | * | 10/2008 | Ishikura | ............ A61M 25/0618 604/198 |
| 2009/0054852 A1 | * | 2/2009 | Takano | ................. A61M 5/158 604/263 |
| 2010/0222746 A1 | * | 9/2010 | Burkholz | .......... A61M 25/0606 604/164.08 |
| 2012/0184910 A1 | * | 7/2012 | Woehr | ............. A61M 25/0606 604/164.08 |
| 2013/0060198 A1 | | 3/2013 | Woehr et al. | |

OTHER PUBLICATIONS

Written Opinion for corresponding PCT Application No. PCT/EP2014/055086 filed Mar. 14, 2014, from International Searching Authority (EP) dated May 30, 2014 (4 pages).

* cited by examiner

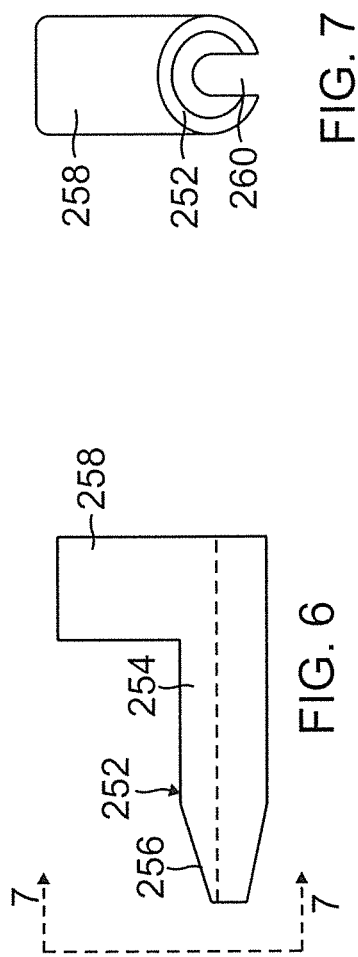
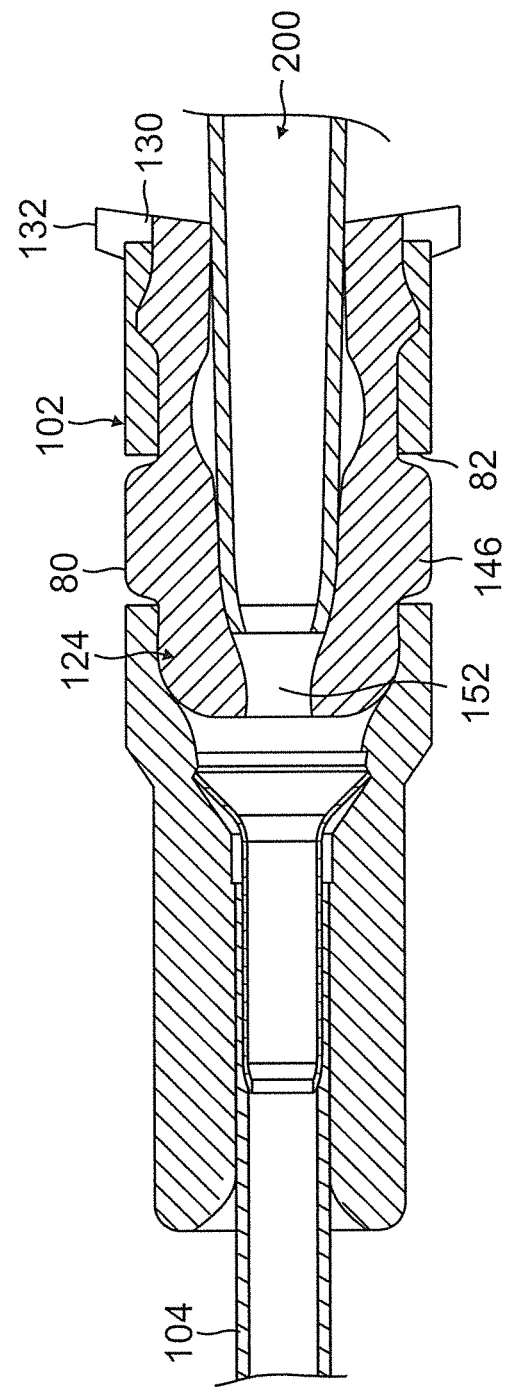

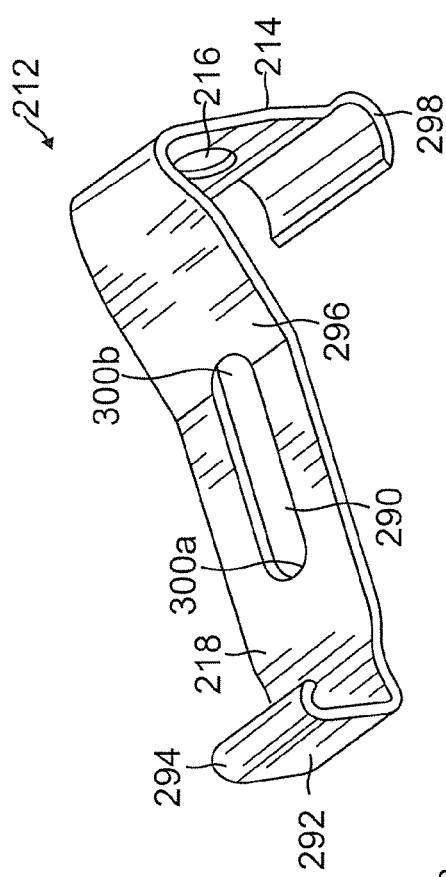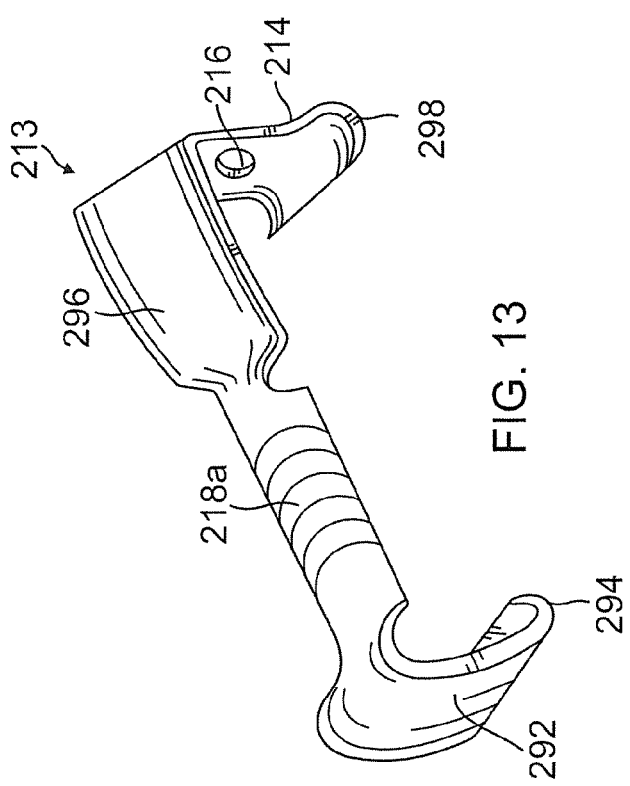

CATHETER ASSEMBLIES WITH WIPEABLE BLOODSTOP AND RELATED METHODS

FIELD OF ART

Catheter assemblies are generally discussed herein for intravenous venipuncture with more specific discussions related to IV catheter assemblies having wipeable bloodstops, septums, or valves in combination with tip protectors for covering the needle tips.

BACKGROUND

Insertion procedure for an IV catheter (IVC) assembly contains four basic steps: (1) the healthcare worker inserts the needle and catheter together into the patient's vein; (2) after insertion into the vein with the needle point, the catheter is pushed forward into the vein of the patient by the healthcare worker with his or her finger; (3) the healthcare worker withdraws the needle by grasping the catheter hub end while at the same time applying pressure to the patient's vein distal of the catheter to stop the flow of blood through the catheter with his or her free hand; and (4) the healthcare worker then tapes the now inserted catheter to the patient's skin and connects the exposed end of the catheter (the catheter hub) to the source of the fluid to be administered into the patient's vein.

The problem is that immediately after the withdrawal of the needle from the patient's vein, the healthcare worker must place the exposed needle tip at a nearby location and address the tasks required in items (3) and (4) above. It is at this juncture that the exposed needle tip creates a danger of an accidental needle stick, which, under the circumstances, leaves the healthcare worker vulnerable to the transmission of various dangerous blood-borne pathogens, including AIDS and hepatitis from an accidental needle stick.

An additional problem comes if the health care worker inserting the IV catheter stops applying pressure to the vein to use a second hand for step (4) above. This can increase the risk of infection for the patient and causes more work for the health care worker to clean up the blood that may escape from the open catheter hub.

Other needle types similarly expose healthcare workers to risks of accidental needle sticks. For example, a doctor administering an injection, using a straight needle, a Huber needle, a winged infusion needle, etc., may place the used needle on a tray for subsequent disposal by a nurse. For the period between placing the used needle on a tray or a work station to the time it is discarded, the used needle is a potential source for disease transmissions for those that work near or around the needle. Accordingly, all needles should be covered upon withdraw of the needle from the patient to ensure greater worker safety. Ideally, the procedure for covering the needle tip should be passive, self-activating, or at least simple to perform. In addition, the device for covering the needle should be reliable and robust.

IV catheter assemblies are also known to have an in-line valve located in the catheter hub to stop or slow down the flow of blood back flash following successful venipuncture. However, the location or position of the valve relative to the catheter hub makes wiping or cleaning the valve nearly impossible. Additionally, the location of the valve within the catheter hub makes it difficult to incorporate a tip protector or needle guard in addition to having a catheter with a valve that can be wiped.

SUMMARY

Aspects of the present disclosure include a safety IV catheter (IVC) comprising a catheter hub attached to a catheter tube and a needle attached to a needle hub. Said safety IVC further comprising a valve attached to the catheter hub, said valve comprising an interior cavity, a proximal end wall exposed externally of the catheter hub, and a slit formed in the proximal end wall of the valve. The needle extends through the catheter tube and a tip protector comprising a distal end portion, a proximal wall comprising an opening, and a small profile located between the distal end portion and the proximal wall having the needle passing through the opening on the proximal wall. Wherein the distal end portion of the tip protector is located inside the interior cavity of the valve and the proximal wall located externally of the valve.

The safety IVC wherein the small profile can optionally be located at the slit.

The safety IVC wherein the tip protector optionally comprises one substantially flat or two substantially flat arms that cross one another when viewed along a side view and wherein the small profile is located on the on arm or where the two arms cross.

The safety IVC wherein the needle optionally comprises a crimp.

The safety IVC wherein the crimp, if incorporated, is sized larger than the opening on the proximal wall.

The safety IVC wherein the valve extends proximally of the catheter hub.

The safety IVC further comprising an installation tool for mounting the distal portion of the tip protector through the slit. The tool is removable from the assembly after installation of the tip protector.

Aspects of the present embodiment further include a method for manufacturing a safety IV catheter. In an embodiment, the method comprises the steps of forming a catheter hub and attaching the catheter hub to a catheter tube. The method can further include the step of attaching a tip protector having one or two arms on a needle and partially into a valve comprising an interior cavity. The method can further include the step of attaching the valve/tip protector/needle unit to the catheter hub. In some examples, the valve comprises a proximal end wall exposed externally of the catheter hub and a slit. The method can further comprise the steps of forming a needle hub and attaching the needle hub to the needle and extending the needle through the catheter tube. In some examples, the tip protector has a distal end portion, a proximal wall comprising an opening, and a small profile located between the distal end portion and the proximal wall.

The method can further comprise the step of aligning the small profile to sit at the slit of the valve.

The method can further comprise the step of opening the valve with a tool comprising a bore around the needle and around the tip protector before placing a distal portion of the tip protector inside the interior cavity of the valve.

The method can further comprise the step of placing a distal end of the tool in through the slit before placing the tip protector inside the interior cavity of the valve. In some examples, the tool has a distal cutout for accommodating the distal end of the tip protector. In yet other examples, the tool is made from two separate pieces to allow the tool to be inserted into the valve with the two pieces in a collapsed state and then expanding or separating the two pieces to provide space for inserting the tip protector.

The method can further comprise the steps of wiping the proximal end wall of the valve with an antiseptic solution. In some examples, the wiping motion is a single smooth motion across the exterior most proximal surface of the valve, which is exposed and not covered by the catheter hub.

The method wherein the tip protector can comprise two arms that cross one another and wherein the small profile is located where the two arms cross.

The method can further comprise the step of pushing the distal end portion of the tip protector through a bore of the tool. In some examples, the tool comprises a cutout at a distal end for allowing the tip protector to pass through the distal end of the tool.

The method wherein the needle hub can comprise a Luer taper.

The method can further comprise the step of removing the needle from the catheter hub.

A further aspect of the present disclosure is a method for manufacturing a safety IV catheter. In one example, the method comprises the steps of forming a catheter hub and attaching the catheter hub to a catheter tube. The method can further comprise the step of attaching a tip protector with one or two arms on a needle partially into a valve comprising an interior cavity and then attaching the valve/tip protector/needle unit to the catheter hub. In some examples, the valve comprises an interior cavity, a proximal end wall, and a slit at the proximal end wall. The method can further comprise the steps of forming a needle hub and attaching the needle hub to a needle and placing a tool over the needle and at least partially through the slit on the valve, said tool comprising a hollow interior. The method can further comprise the step of inserting the needle through the catheter hub; and placing a tip protector, at least in part, inside the interior cavity of the valve, by sliding the tip protector at least partially through the hollow interior of the tool. Then removing the tool by moving the tool sideways from the needle through a slot on the tool.

The method wherein the valve can comprise a proximal wall and wherein the proximal wall of the valve is located externally of the catheter hub.

The method wherein the tip protector can comprise a distal end portion, a proximal wall comprising an opening, and a small profile located between the distal end portion and the proximal wall.

The method wherein the tool can comprise a lengthwise slit having a dimension larger than a diameter of the needle.

A still further feature of the present disclosure is a safety IV catheter comprising a catheter hub attached to a catheter tube and a needle hub having a needle with a needle diameter extending through the catheter tube. The safety IVC can further comprise a valve attached to the catheter hub, said valve comprising an interior cavity, a proximal end wall located at a proximal end of the catheter hub, and a slit. A tip protector is provided with the valve. The tip protector comprising a distal end portion of a first dimension, a proximal wall of a second dimension comprising an opening having an opening dimension, and a center section of a third dimension located between the distal end portion and the proximal wall, the third dimension is smaller than the needle diameter; and wherein the distal end portion of the tip protector is located inside the interior cavity of the valve and the proximal wall located externally of the valve.

A safety IV catheter substantially as shown in the figures and described in the specification.

BRIEF DESCRIPTION OF THE DRAWINGS

These and other features and advantages of the present device, system, and method will become appreciated as the same becomes better understood with reference to the specification, claims and appended drawings wherein:

FIG. 6 is a side elevation view of a needle installation tool provided in accordance with aspects of the present disclosure.

FIG. 7 is a front view of the needle installation tool of FIG. 6.

FIG. 8 is a schematic cross-sectional side view of the catheter assembly of FIG. 1 in use with a male implement.

FIG. 12 is an isometric view of the tip protector shown in the catheter assembly of FIG. 9.

FIG. 13 is an isometric view of an alternative tip protector provided in accordance with aspects of the present disclosure, which is usable with the catheter assemblies discussed herein.

DETAILED DESCRIPTION

The detailed description set forth below in connection with the appended drawings is intended as a description of the presently preferred embodiments of safety IVCs (intravenous catheters) provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
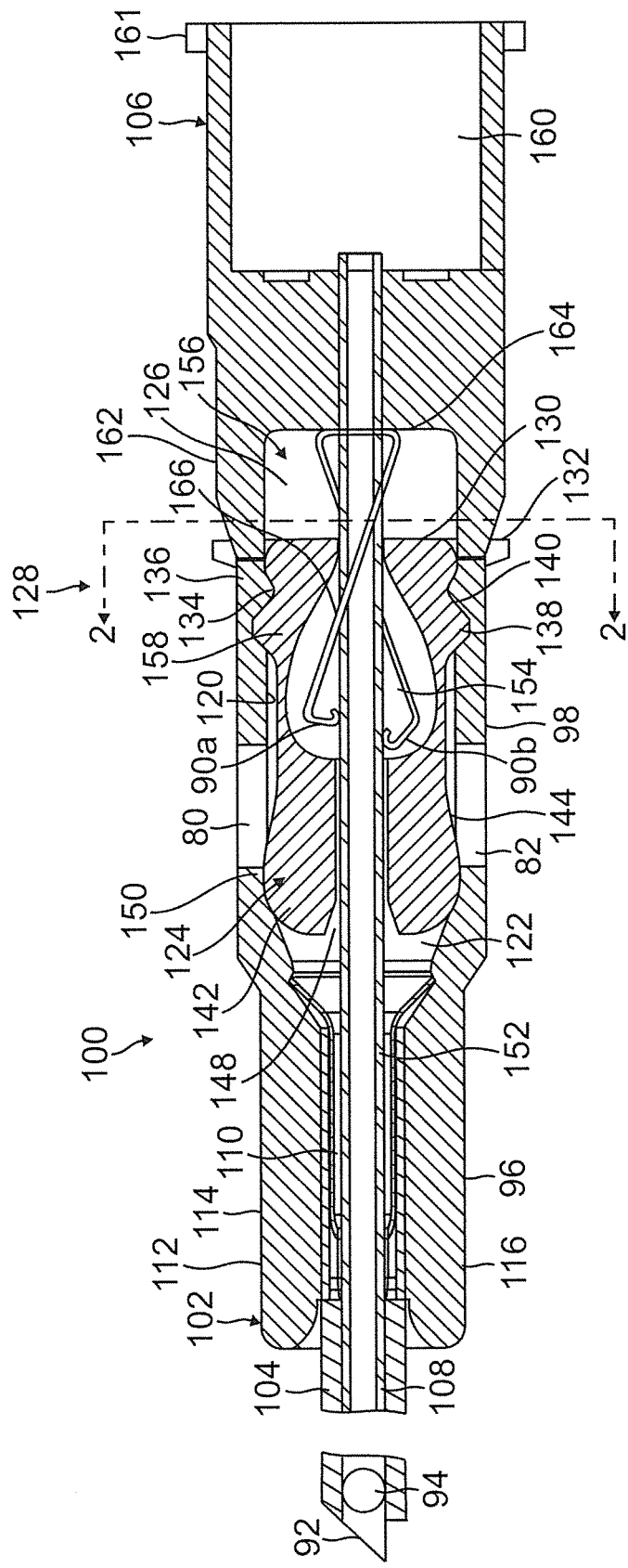
FIG. 1 is a schematic cross-sectional side view of a catheter assembly with a valve provided in accordance with aspects of the present disclosure.

With reference to FIG. 1, a cross-sectional side view of a safety IVC 100 is shown, which comprises a catheter hub 102 comprising a catheter tube 104 and a needle hub 106 comprising a needle 108 projecting through the catheter tube in the ready to use position. The catheter tube 104 is held to the catheter hub 102 by a retaining member 110, which wedges the proximal end of the tube against the interior surface of the nose section 112 of the catheter hub and is well known in the art. The catheter hub 102 is further shown with a body 114 having an exterior surface 116 with an optional gripping projection (not shown) to enable a finger or several fingers to push there-against for leverage during use or during withdrawal of the needle hub following successful venipuncture. The safety IVC 100 may be sized with different sized needles and catheter tubes, such as 14 gauge, 16, gauge, 18 gauge, etc., and with different lengths for central venous applications, arterial venous applications, or intravenous applications. In one example, the catheter hub 102 is formed with a distal hub section 96 and a proximal hub section 98 that connect together using two or more side tabs or wall sections (not shown), such as by welding or gluing the side tabs of one hub section to another hub section. In one example, the side tabs are located on the distal hub section. In another example, the side tabs are located on the proximal hub section. By attaching the distal hub section 96 and the proximal hub section 98 using side tabs, the hub 102 is left exposed along an upper open section 80 and a lower open section 82, which may be referred to as first and second hub body openings, respectively. The first and second hub body openings 80, 82 allow the valve to expand there into during use when a male implement, such as an IV line, is inserted therein. In some examples, the hub has only one opening, either opening 80 or 82. In still other examples, the hub is sized and shaped to ensure sufficient clearance to permit the valve to expand without incorporating any hub body opening. Optionally, an outer sleeve (not shown) may be positioned over the catheter hub 102 to cover the two hub body openings 80, 82. For example, an elastomeric sleeve, which can be a rubber material or a silicone material, may be slid over the outer exterior surface of the catheter hub to cover the two hub body openings.

Interiorly, the catheter hub 102 comprises an interior surface 120 defining an interior cavity 122 having an elastic valve 124 located therein. The valve 124 may also be referred to as a seal, a septum, or a blood stop and its function is, among other things, to stop or restrict the flow of blood flashback into the interior cavity 122 and out the proximal end 126 of the catheter hub following successful venipuncture. With the elastic valve 124, secondary blood flashback can readily flow in the gap between the catheter tube 104 and the exterior surface of the needle 108 up to the interior cavity 122. Additionally, when the needle 108 and the needle hub 106 are removed from the catheter hub following successful venipuncture, the backflow of blood will stop as the elastic valve 124 closes automatically.

As shown, the elastic valve 124 is positioned at the proximal end 128 of the catheter hub 102 with the proximal valve surface 130 flush, concave (as shown in FIG. 1), convex or exposed at the proximal end 128 of the catheter hub for wiping and/or cleaning, such as for cleaning the surface with an antiseptic solution. The valve surface 130 is exposed, similar to a table top, for easy wiping and cleaning without having to use special swabs or tools to reach hard to get crevices. In one example, the elastic valve 124 incorporates a proximal flange 132 having the noted proximal valve surface 130 for wiping and an exterior annular groove 134. The groove 134 is sized and shaped to mate with an annular projection 136 on the catheter hub body to secure the two together. In another example, the elastic valve or seal 124 incorporates an annular projection 138 for engaging an annular groove 140 on the catheter hub to secure the two together. In yet another example, the elastic valve incorporates both an annular groove and an annular projection to engage with corresponding features on the catheter hub. Additionally or alternatively, a distal enlarged section 142, which can be an enlarged distal head or a ring projection extending radially outwardly of the valve body 146, is provided for engaging the catheter hub at the distal end of the elastic valve. If incorporated, this provides an additional engagement point between the elastic valve and the catheter hub. The distal engagement can instead be the single engagement point between the elastic valve and the catheter hub without also engaging at the proximal end of the valve with the catheter hub. Still alternatively, the distal engagement on the valve body 146 may embody a recess or groove for receiving a corresponding projection formed in the interior cavity of the catheter hub.

To facilitate inserting the elastic valve 124 into the interior cavity 122 of the catheter hub 102, a recessed mid-section 144 is incorporated to provide clearance during insertion of the elastic valve 124. The recessed mid-section 144 has a cross-sectional dimension that is smaller than cross-sectional dimension of the projection 138 on the elastic valve. In another example, the recessed mid-section 144 has a cross-sectional dimension that is smaller than the cross-sectional dimension of the groove 134 on the elastic valve, if incorporated. In still yet another example, the recessed mid-section 144 has a cross-sectional dimension that is smaller than the cross-sectional dimension of the projection or enlarged distal section 142 on the elastic valve, if incorporated. Once installed, the recessed mid-section does not contact the interior surface of the catheter hub. As further discussed below, the recessed mid-section 144 is sized and shaped to provide a space or gap to enable the valve body 146 to expand when a male implement, such as a drip line, a male Luer, or a syringe tip, is inserted into the elastic valve to perform a medical procedure.

To further facilitate inserting the elastic valve 124 into the interior cavity 122 of the catheter hub 102, a distal central recessed section 148 may be incorporated in or on the elastic valve body 146 to allow the distal end to compress during insertion or during installation. This allows the distal end of the elastic valve to squeeze into the interior cavity of the catheter hub to engage the distal enlarged section 142 with the annular distal recessed section 150 of the catheter hub, if the second engagement is incorporated. In another example, the distal central recessed section 148 is omitted and only a slit is formed at the distal end of the valve, as further discussed below. If omitted, space for the expanding valve inside the catheter hub can be accommodated by a properly sized and shaped catheter hub. In one example, the catheter hub may be made from multiple hub parts, such as two or more hub parts, to facilitate mounting the elastic valve to the hub, as further discussed below.

In an example, the elastic valve 124 is made from an elastomer, such as a rubber material or silicone. The elasticity of the valve is inherent in the material selection and can be adjusted or modified through manufacturing techniques, such as by adjusting the durometer or hardness. Alternatively, a thermoplastic elastomer (TPE) may be used to form the elastic valve. Exemplary TPEs include those that come from block copolymers group such as Arnitel from DSM Company, Solprene from Dynasol, Engage from Dow Chemical, Hytrel from Du Pont, Dyflex and Mediprene from ELASTO, and Kraton from Shell Chemical. In some examples, antimicrobial compositions are provided with the elastic valve for controlling or combating bacterial contamination inside the valve, such as reducing the amount of biofilm formation. In one specific aspects of the present disclosure, silver zirconium phosphate is formulated into the molding material for molding the elastic valve 124, i.e., added to the TPE, silicone, or rubber material. The silver compound may vary between about 1% to about 10% by weight of the elastomer or TPE with a preferred range of between about 6% and about 8%. Alternatively or in addition thereto, antimicrobial compositions are blended in the materials for molding the catheter hub. Other antimicrobial agents useable with the components of the present systems, devices, and methods include: silver, gold, platinum, copper, and zinc. Antimicrobial metal compounds used herein include oxides and salts of preferably silver and also gold, for example: silver acetate, silver benzoate, silver carbonate, silver citrate, silver chloride, silver iodide, silver nitrate, silver oxide, silver sulfa diazine, silver sulfate, gold chloride and gold oxide. Platinum compounds such as chloroplatinic acid or its salts (e.g., sodium and calcium chloroplatinate) may also be used. Also, compounds of copper and zinc may be used, for example: oxides and salts of copper and zinc such as those indicated above for silver. Single physiological, antimicrobial metal compounds or combinations of physiological, antimicrobial metal compounds may be used. Still alternatively, a thin antimicrobial agent may be deposited over a wall surface of the catheter components. Other antimicrobial agents useable with the elastic valve include chlorhexidine gluconate, chlorhexidine diacetate, chloroxylenol, povidone iodine, Triclosan, benzethonium chloride, benzalkonium chloride, octenidine, and antibiotic.

With reference again to the elastic valve 124 of FIG. 1, a through bore 152 is provided between the two ends of the elastic valve, i.e., between the distal end and the proximal end. The through bore 152 provides a path for the needle 108 when assembling the needle hub 106 to the catheter hub 102 and for fluid flow when connected with a male Luer, a needle, or a male implement through the valve, as further discussed below. Additionally, an enlarged interior bore section 154 is formed inside the elastic valve 124 and in communication with the through bore 152. In the example shown, the enlarged interior bore section 154 is shaped as a tear drop with the smaller end of the shaped cavity located at the proximal end of the valve and a rounder and larger end more distally of the valve. The enlarged interior bore section 154 is sized and shaped to accommodate at least part of a tip protector or needle guard 156, which is partially located inside the elastic valve 124 and partially located outside the elastic valve. Thus, the elastic valve 124 is understood to comprise an elastomeric body or a TPE body having a through bore formed between a distal end and a proximal end and having a first cross-sectional dimension. An enlarged interior bore section having an interior surface and in communication with the through bore is further provided with the valve, said enlarged interior bore section having a cross-sectional dimension, for example a second cross-sectional dimension, that is at least two times (i.e., 2×) the first cross-sectional dimension for accommodating at least a portion of a tip protector. In other examples, the second cross-sectional dimension is at least two times the first cross-sectional dimension when the first cross-sectional dimension is opened by a male implement.

In some examples, the enlarged portion of the tear drop shape cavity is sufficiently large to accommodate the needle guard without touching the needle guard. However, some touching between the needle guard and the interior cavity of the enlarged interior bore section 154 is contemplated. In an example, the enlarged interior bore section is located between the proximal end and the distal end. In some examples, the enlarged interior bore section is located proximally of the through bore through the distal valve section. In an example, the enlarged interior bore section has a tear drop shape with the smaller end 158 of the tear drop shape located closer to the proximal end of the elastic valve than the distal end of the elastic valve 124. The smaller end 158 can be defined at least in part by the proximal flange 132, which has an opening, such as a slit, having a perimeter that touches the needle 108 and/or the tip protector 156, as further discussed below. The larger end of the tear drop shape is sized and shaped to accommodate the tip protector without touching the tip protector so as to not interfere with the movement of the tip protector, as further discussed below. In some examples, the needle guard touches the enlarged interior bore section 154.

In one example, the elastic valve 124 is formed from a single core pin having an enlarged section having a shape of a tear drop for forming the enlarged interior bore section 154. The core pin can be removed through a small gap in the flange 132 by expanding the proximal flange 132. Later when the elastic valve 124 is press fit into the catheter hub, the gap is closed to a slit. The opposite end can be slit with a blade. Alternatively, the enlarged interior bore section 154 can be formed from two core pins meeting at the largest point inside diameter and both leaving a small gap on both ends that is then press fit into the catheter hub to close the gap to a slit. Still alternatively, the elastic valve 124 can be formed in two halves split along the largest inside diameter of the interior bore section 154. There can alternatively be overlapping of the two elastic valve halves. After forming and curing the two halves, they both can be slit with a blade. Yet a further alternative forming technique for forming the enlarged interior bore section 154 is blow molding leaving a small gap on one end or the other which is pressed closed to a slit. The opposite end can be slit with a blade.

The needle hub 106 is shown comprising a flash chamber 160 and exterior threads 161, which chamber can be sized as a female Luer. An air permeable vent plug may be positioned at the proximal opening of the flash chamber of the needle hub to stop blood flow when the catheter assembly is in use, such as following successful venipuncture. Additionally, a distal shroud 162 is incorporated at the distal end of the needle hub for receiving or accommodating the proximal clip section of the tip protector. The shroud 162 has a base wall 164 of a depth that is sized to accommodate the tip protector 156 without pushing the tip protector too far distally so that the narrowest point, reduced point, or the intersection 166 of the tip protector 156 is not displaced from the end opening of the elastic valve by the base wall when assembled. In certain embodiments, the guard can be positioned away from its narrowest point at the slit.

As shown, part of the tip protector 156 extends proximally externally of the valve and positioned in the distal shroud 162 of the needle hub. In one example, the part that extends externally comprises a proximal wall comprising an opening, which has the needle passing therethrough. In other examples, the part of the tip protector that extends externally of the valve can embody a different shape, such as having a proximal section comprising two or more walls, comprising an irregular shaped wall, or comprising multiple different materials. The needle 108 extends distally of the distal shroud 162 and terminates in a needle tip 92, which has a sharp puncturing end, and a needle change in profile 94, which can be a crimp, a bulge, a sleeve attached to the needle, or a material build up. The change in profile 94 is configured to cooperate with the needle guard 156 to prevent the guard from falling distally off of the needle, such as by engaging the circumference of the opening on the proximal wall of the tip protector. In other embodiments, the change in profile can be omitted and the guard forms a snap fit around the shaft to prevent the guard from falling distally off of the needle. For example, the guard can have an opening having the needle project therethrough when not activated and wherein the needle guard snaps or pivots to grip the needle. As shown, the tip protector 156 has two arms 90a, 90b that cross and is similar to one of the needle guards or tip protectors disclosed in U.S. Pat. No. 6,616,630, the contents of the '630 patent are expressly incorporated herein by reference. While the guard 156 is shown as a unitary component, it may be made from multiple components that are assembled together and cooperate to cover or protect the needle tip 92 from inadvertent needle sticks. At the point where the two arms 90a, 90b cross, the tip protector defines a smallest profile when viewed in the cross-sectional side view. The smallest profile may also be referred to as the narrowest point, the reduced point, or the intersection 166. As shown, the reduced point 166 is positioned at the slit 168 of the elastic valve 124, which may have several sectional slits forming the slit of the elastic valve as further discussed below with reference to FIG. 2.

By positioning smallest profile of the tip protector at the slit 168, the valve 124 can almost close completely at the slit even in the ready position of FIG. 1. Thus, one advantage of having a needle tip guard 156 with a varying contour is to permit the smallest portion 166 of the varying contour to be located at the slit 168 so as to minimize the physical opening of the slit in the ready position. The smallest portion 166 on the needle guard 156 also represents a self-centering point since the arms converge at the narrow point, which allows the flaps at the slit to ease, uncoil, or settle in the tapering direction of the converging portion.

Thus, the catheter assembly provided herein is understood to include a catheter hub with a catheter tube and a needle hub with a needle and having an elastic valve positioned inside the catheter hub and distal or overlapping with a distal end of the needle hub with the needle projecting through the valve and the catheter tube. The valve has a through bore and an enlarged interior bore section having an interior surface and in communication with the through bore. In one example, the enlarged interior portion has a tear drop shape. In another example, the shape is a flattened tear drop shape. In still yet another example, the shape is generally oblong with optional pointed or narrow points or ends at the longer dimension of the oblong shape. The enlarged interior bore section having a cross-sectional dimension for accommodating at least a portion of a tip protector. In some examples, the enlarged portion of the tear drop shape cavity is sufficiently large to accommodate the needle guard without touching the needle guard. In some examples, the tear drop shape cavity is contoured to closely match the contour of the needle guard, which has a smallest portion located at or near the smallest point of the tear drop cavity. However, some touching between the needle guard and the interior cavity of the enlarged interior bore section 154 is contemplated. In an example, the needle guard is partially projected into the valve positioned in the enlarged interior bore section 154, which is located inside the valve. As discussed elsewhere herein, the enlarged interior bore section is located proximally of the through bore through the distal valve section and is located between the proximal end and the distal end of the elastic valve. The needle guard further has a proximal portion projecting proximally from the valve. In the example shown, the proximal section of the tip protector or guard that projects externally of the valve is located in a shroud at the distal end of the needle hub.

Figure 2:
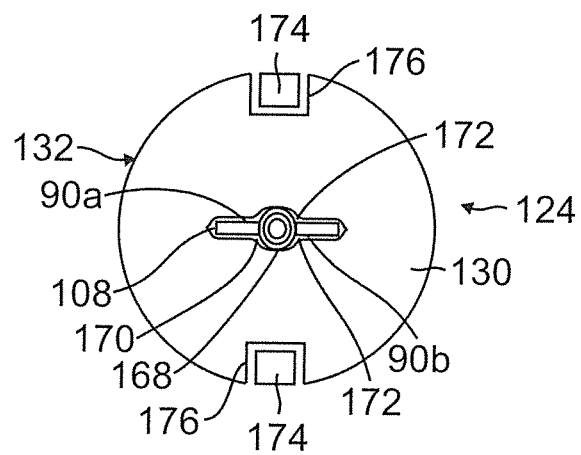
FIG. 2 is a sectional end view of the catheter assembly of FIG. 1 taken along line 2-2.

With reference now to FIG. 2, an end view of the catheter assembly 100 taken at line 2-2 of FIG. 1 is shown. As shown, the slit 168 on the proximal valve surface 130 is made by forming a horizontal cut 170 to create upper and lower flaps 172. In one example, additional cuts are included in addition to the horizontal cut 170. In yet other examples, two or more than three cuts are made to form the slit 168. The cuts can be equally spaced around the central point on the proximal valve surface 130. The needle 108 and two of the anus 90a, 90b of the needle guard 156 can be seen at the slit.

Also shown in FIG. 2 are two axially extending tabs 174 that project from the distal shroud 162 of the needle hub 106. The axially extending tabs 174 align and project into corresponding notches 176 formed in the proximal flange 132 of the elastic valve 124. This arrangement allows the needle hub to align with the catheter hub and limit relative rotation between the two. The axially extending tabs 174 also establish an exact actual position between the harder portions of the catheter hub, such as an end surface of the catheter hub body, and the needle hub, such as the extending tabs 174. By having two relatively harder or stiffer surfaces contact as a reference point for axial alignment, this helps to set the needle tip as close as possible to the catheter tube tip or end of the catheter tube. Thus, the position of the proximal end surface of the elastic valve 124 can vary without affecting the lie distance between the needle bevel and the catheter tube tip, which should be kept to a minimum. In an alternative embodiment, only a single axially extending tab 174 and a single notch 176 are used to provide the alignment function. In an alternative embodiment, the notch or notches 176 and the corresponding tab or tabs 174 may be eliminated and the alignment, both axially and angularly, may be provided by incorporating extensions around or over the flange 132 on the valve so that the alignment is provided around or over the flange.

Figure 3A:
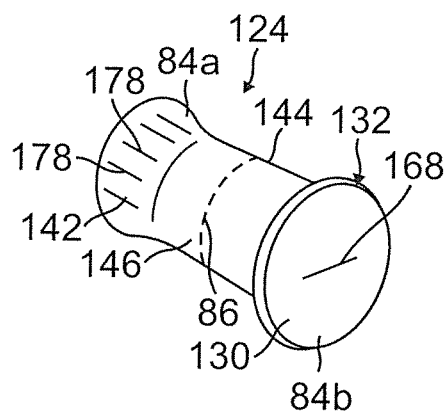
FIG. 3A is an isometric view of a valve or septum provided in accordance with aspects of the present disclosure.

FIG. 3A is an isometric view of an exemplary elastic valve 124 provided in accordance with aspects of the present disclosure. In one example, a plurality of micro channels, bumps, or protrusions 178, which define vent paths, are formed at or on the distal enlarged section 142 of the elastic valve. The vent paths provide venting to facilitate secondary blood flashback as described earlier. In another example, helical or spiral paths are formed on the enlarged section 142 to provide helical or spiral vent paths. In an alternative embodiment, the valve body 146 does not have a distinct recessed mid-section 144 to provide a gap inside the catheter hub for expansion. Instead, the body is generally constant and the catheter hub is provided with a recessed space to provide the expansion space. Alternatively, there are no vents formed on the outside of the elastic valve body but on the inside of the catheter hub, where it mates with the elastic valve. The vents between the outside of the elastic valve and catheter hub are optional and may be omitted when vents between the needle and the elastic valve are provided. In other words, vents may be formed on either side of the needle where the slits do not close completely due to the presence of the needle and the relative geometries of the needle and the slit.

In one example, the valve 124 is made from two separate valve sections, such as a distal valve section 84a and a proximal valve section 84b, which have a radial split line 86. The two valve sections 84a, 84b can overlap in the middle to form a seal. A two part elastic valve will allow the enlarged bore section to be readily formed by the core pins and the core pins readily removed. When the valve 124 is made of two halves, then the slits on either end can be post-mold manipulated, such as by cutting with a blade.

Figure 3B:
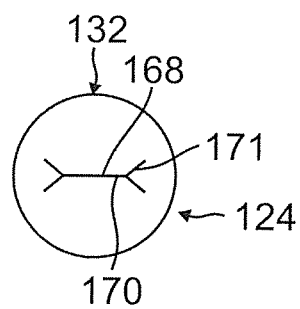
FIG. 3B is an end view of the valve or septum of FIG. 3a with an alternative slit.

FIG. 3B is an end view of an alternative slit 168. As shown, a horizontal cut 170 and diagonal corner cuts 171 are provided to accommodate the needle and portions of the arms that extend through the slit 168.

Figure 3C:
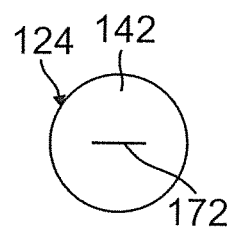
FIG. 3C is a front view of the valve or septum of FIG. 3a showing a front slit formed through the distal enlarged section.

FIG. 3C is a front end view of the elastic valve 124. As shown, a front slit 170 is provided through the distal end of the elastic valve 124. This allows the valve to be mounted over the needle, or the needle to project through the valve, in the ready to use position of FIG. 1. Likewise, slit 172 can also have diagonal corner cuts 171.

Figure 4:
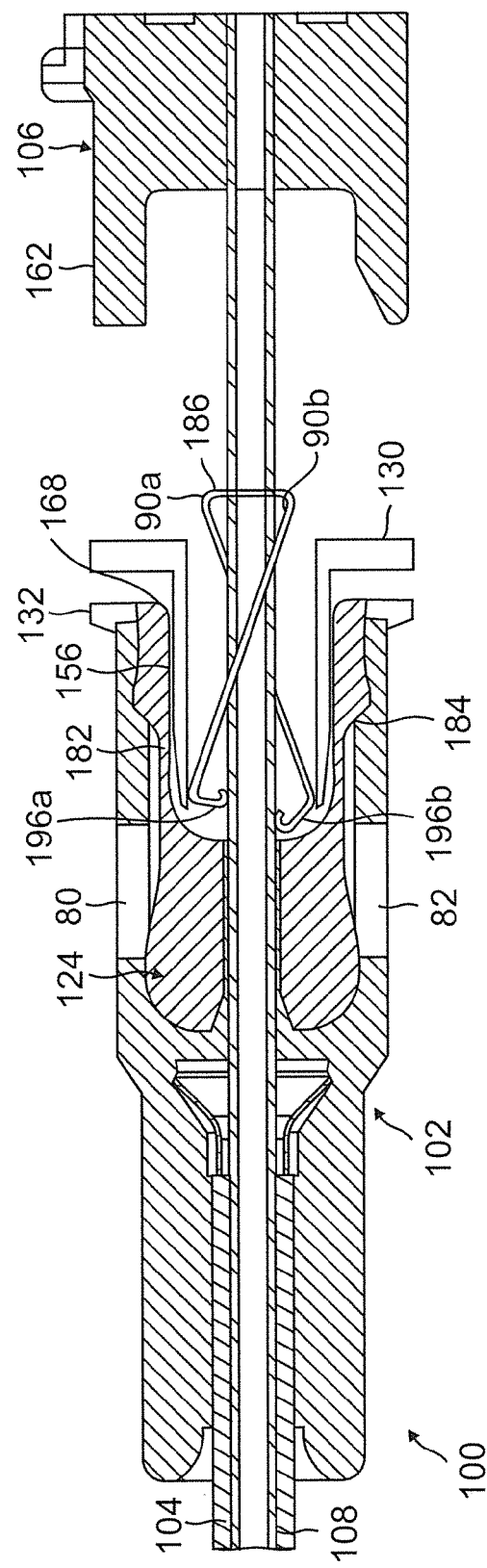
FIG. 4 is a schematic cross-sectional side view of the catheter assembly of FIG. 1 in a stage of assembly with an installation tool.

FIG. 4 is a schematic cross-sectional side view of the catheter assembly 100 of FIG. 1 in a partially assembled state. As shown, the needle hub 106 is retracted away from the proximal end of the catheter hub to provide clearance for an installation tool 182. The tool 182 is utilized to open up the elastic valve 124 for positioning the tip protector 156 partially through the flange 132. In one example, the installation tool 182 is wedged in through the slit 168 of the elastic valve 124 to open up the enlarged interior bore section 154 of the elastic valve. The needle guard 156 is then slid distally along the needle shaft 108 into the interior space 184 of the installation tool. The tool 182 can be removed by holding the proximal wall 186 of the needle guard, which has a proximally facing wall surface, a distally facing wall surface, and an opening formed therein and/or by holding the arms 90a, 90b, while moving the tool 182 proximally, such as by grabbing the flange 240 on the tool and moving the tool proximally. After the tool 182 separates from the guard, it can slide laterally away from the needle 108. If the installation tool 182 is a two-piece tool, both pieces can separate and move away from the needle. If the tool is a single piece, then a lengthwise gap is provided on the tool to separate the tool from the needle via the gap, as further discussed below. In another embodiment, not shown in FIG. 4, the needle and the tip protector are inserted into the elastic valve before the elastic valve is inserted into the catheter hub. This will allow the tool to expand the elastic valve even more readily than if the valve was preassembled into the catheter hub first before placing the tip protector into the enlarged bore section.

Figure 5:
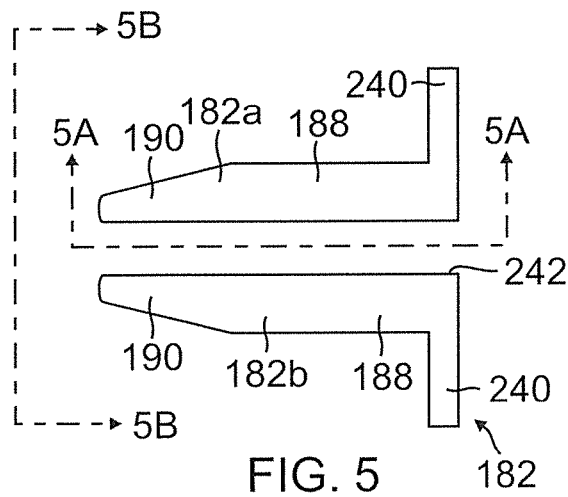
FIG. 5 is a side elevation view of an installation tool provided in accordance with aspects of the present disclosure.

FIG. 5 is a side elevation view of the tool 182 of FIG. 4. As shown, the tool 182 comprises two separate tool components 182a, 182b. Each tool component has an elongated body 188, a tapered nose section 190, a flange 240, and a lengthwise edge 242. When the lengthwise edges 242 of the two tool components 182a, 182b mate, contact, or otherwise come closer together, they form a low profile to allow the tool to readily penetrate the slit 168 in the valve to open up the through bore for installing the needle guard. The two tool components 182a, 182b may be spread apart manually after being inserted through the slit to provide the needed space for installing the needle guard. Alternatively, the two components 182a, 182b may be secured to or be part of a device, such as automated mechanized equipment, used to separate them to create the gap for the tip protector or needle guard and to push the needle guard into the enlarged interior bore section 154.

Figure 5A:
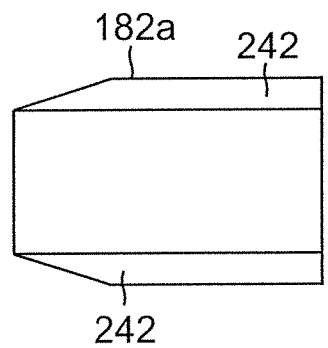
FIG. 5A is a view of one half of the tip protector installation tool of FIG. 5 taken along line 5A-5A.

FIG. 5A is a side view of one of the tool sections 182 of FIG. 5 taken along line 5A-5A. This shows an axial groove running along the entire length of the tool.

Figure 5B:
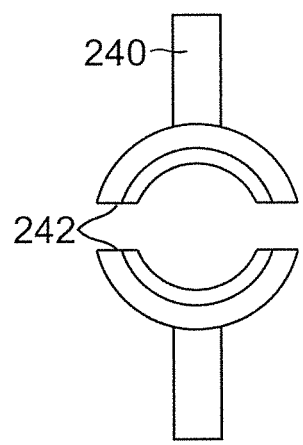
FIG. 5B is a front view of the tip protector installation tool of FIG. 5 taken along line 5B-5B.

FIG. 5B is a front end view of the assembly tool 182 of FIG. 5 taken along line 5B-5B. As shown, each tool has a body section 188 that is generally partially elliptical or oval. In another example, the body section is generally partially round. The assembly tool 182 may be made from a hard plastic or from a non-oxidizing metal material.

Figure 5C:
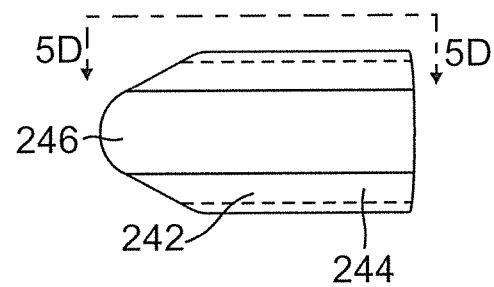
FIG. 5C is a side elevation view of an alternative installation tool provided in accordance with another aspect of the present disclosure.

FIG. 5C is a side view of an alternative assembly tool 242 provided in accordance with aspects of the present disclosure. The alternative tool comprises a tool body 244 comprising a generally cylindrical shape having a gap or channel 246 running the length of the tool body. In other examples, the tool body has a different shape, such being oblong. The assembly tool 242 further comprises a tapered nose section 248. The cylindrical tool body defines an interior space or cavity that is sized and shaped to accommodate a tip protector or needle guard without unduly compressing or squeezing the guard. In another example, the guard can pass through the interior space of the tool without touching the tool.

Figure 5D:
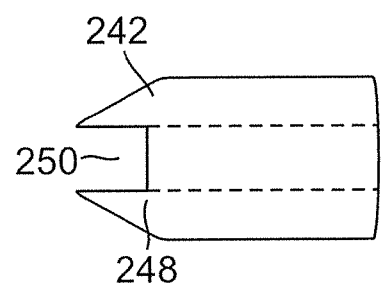
FIG. 5D is a top view of the installation tool of FIG. 5C taken along line 5D-5D.

FIG. 5D is a top view of the tool 242 of FIG. 5C taken along line 5D-5D. As shown, the tapered nose section 248 has two cut-outs 250, one on each side of the channel 246 of FIG. 5D. The two cut-outs 250 are sized and shaped to allow or permit the needle guard to pass therethrough. For example, the cut outs 250 are sized to allow the distal walls 196a, 196b and proximal wall of the needle guard to pass therethrough.

In use, the alternative tool 242 is first placed onto the needle 108 via the channel or gap 246. The tool 242 is then pushed forward so that the tapered nose section 248 opens the slit on the valve and then the slit gradually expands as the tool body 244 enters the slit and the enlarged interior cavity. The guard, which is already mounted on the needle and the needle already inserted through the valve, is then slid through the opening of the tool 242 and partially into the elastic valve. The tool is then retracted proximally over the proximal wall to clear the guard by means of cut outs 250 and then subsequently moved laterally away from the needle through the gap 246 before the needle and needle hub are pushed distally until the extending tabs 174 on the needle hub seat in the cut outs 176 of the valve and hit the proximal end surface of the hard portion of the catheter hub. At this point the needle tip will be extending from the hollow catheter. The tool 242 of FIGS. 5C and 5D may also be used to install the needle guard into the valve before the valve is inserted into the catheter hub, as previously discussed.

FIG. 6 shows a side view of a needle tool 252 provided in accordance with aspects of the present disclosure. In one example, the needle tool 252 comprises a body 254 comprising a tapered nose section 256 and a flange 258. The needle tool 252 is sized and shaped to open the through bore of the elastic valve to enable installation of the needle through the valve and through the catheter tube. The needle tool 252 is configured to be used first to install the needle through the elastic valve before using the guard installation tool 182 or 242 to mount or install the needle guard into the elastic valve. In one example, the needle tool 252 is selected with a sufficient length to open the elastic valve and provide a clear pathway through the through bore and the distal slit of the elastic valve for installing the needle. The needle tool may be made from a hard plastic or a metal material.

FIG. 7 is a front end view of the needle tool 252 of FIG. 6 taken along line 7-7. The tool has a slot, channel, or gap 260 that extends lengthwise through the body 254 and through part of the tapered nose section 256. The gap 260 is sized and shaped to enable mounting the tool 252 over the needle and sufficiently large to allow the change in profile 94 near the needle tip to pass therethrough. This size configuration of the gap allows the change in profile to slide distally thereof during installation and the lengthwise gap 260 allows the needle tool to be removed laterally away from the needle. This tool can be used to insert the needle through the elastic valve before or after the elastic valve is assembled into the catheter hub.

Thus, the catheter assembly provided herein is understood to include a catheter hub with a catheter tube and a needle hub with a needle and having an elastic valve positioned inside the catheter hub and distal of the needle hub with the needle projecting through the valve and the catheter tube. The valve has an enlarged interior bore section having an interior surface and in communication with a through bore formed in the valve, such as through a distal valve section of the elastic valve. The enlarged interior bore section having a cross-sectional dimension for accommodating at least a portion of a tip protector. As shown, an installation tool comprising a lengthwise gap may be inserted through the slit on the valve to form an installation pathway for inserting the distal end of the guard into the interior of the valve. Subsequently, the installation tool can move proximally on the needle and then laterally to separate the tool from the needle, via the lengthwise gap. In some examples, the installation tool is formed from two separate pieces that are first brought together to insert through the slit of the elastic valve. Once inside, the two separate pieces are separated to provide a pathway for mounting the needle guard.

A further aspect of the present disclosure is understood to include a needle installation tool for installing a needle through an elastic valve and a guard installation tool for installing a guard partially in the elastic valve. Preferably, the needle tool is used first to install the needle and then the guard installation tool is used to install the needle guard. Thus, a method in accordance with aspects of the present disclosure is understood to include the steps of using a needle tool to install a needle through a valve and through a lumen of a catheter tube, and using a guard installation tool to install a needle guard partially in an enlarged interior bore section of the elastic valve such that the needle guard is located partially inside the valve and partially outside the valve. The method can further comprise the step of mounting the needle guard inside the valve so that a reduced section of the guard is located at a slit on the valve. The method can further include mounting the valve inside a catheter hub such that a proximal wall surface of the valve, which has an enlarged interior bore section in communication with a through bore of a smaller cross sectional dimension, is located exteriorly of the catheter hub to facilitate antiseptic cleaning of the proximal wall surface. The catheter hub may include one or more side openings to accommodate the valve when the valve is expanded by a male implement, such as an IV tip, a luer tip, or a syringe tip.

FIG. 8 is a cross-sectional side view of the catheter of FIG. 1 after successful venipuncture and after the needle, the needle guard protecting the needle tip, and the needle hub have been retracted, as described in U.S. Pat. No. 6,616,630. At that point, the slit 168 on the elastic valve 124 closes the opening at the proximal wall surface 130 to stop or limit any blood or fluid leakage out through the slit. The catheter hub 102 is now ready to receive medicinal fluid, intravenous fluid, or infusion fluid. Alternatively, a blood sample may be drawn through the catheter hub by attaching a syringe or blood collection adapter with male luer tip and then pushing a vacuum tube onto the adapter. Additionally or before any of the described steps are taken, the valve 124 provides an exposed proximal wall surface 130 that can be wiped and antiseptically cleaned by simply wiping across the exposed surface of the proximal wall with a cleaner, such as with a pre-moistened swab, a cotton ball, a prep pad, a swab pad, or the likes. The wall surface 130 is unobstructed and therefore can be cleaned without having to clean corners or crevices of the elastic valve compared to when the valve is not fully exposed at the proximal end of the catheter hub 102, such as being recessed inside the catheter hub.

As shown, a male implement 200, such as a male Luer, a syringe tip, a spike, or other medical connector, is pushed through the slit at the proximal wall surface 130 of the proximal flange 132 of the valve. The male implement 200 is understood to be connected to a fluid source, a tubing, or both. The size of the male implement forces the through bore 152 to expand outwardly and part of the valve body 146 to expand and fill the interior cavity of the catheter hub and out the hub openings 80, 82. A seal is formed between the exterior surface of the male implement 200 and the through bore, which is formed by the elasticity of the valve material squeezing against the exterior surface of the male implement. In another embodiment, the elastic valve 124 expands but is confined within the body or within the interior cavity of the catheter hub, which has being oversized to accommodate the expanding valve without any hub opening. Alternatively, an outer sleeve may be provided to cover the openings 80, 82 so that when the valve expands, no part of the valve is exposed. The sleeve can also contain any secondary flashback to within the interior of the catheter hub.

The valve 124 is capable of repeated use. For example, the male implement 200 may be removed following use, such as for changing out the fluid source when emptied and replaced with a new fluid source or when a blood collection device is attached by a standard male luer taper, and the elastic valve 124 will automatically close its slit 168 at the proximal end to stop or limit leakage proximally out through the valve. In some examples, the valve body 146 recoils and closes off the through bore 152 upon removal of the male implement. In yet other examples, a syringe may be used to inject medicine through the catheter device or draw fluid out the catheter device. When the syringe is removed, the through bore 152 automatically closes.

Figure 9:
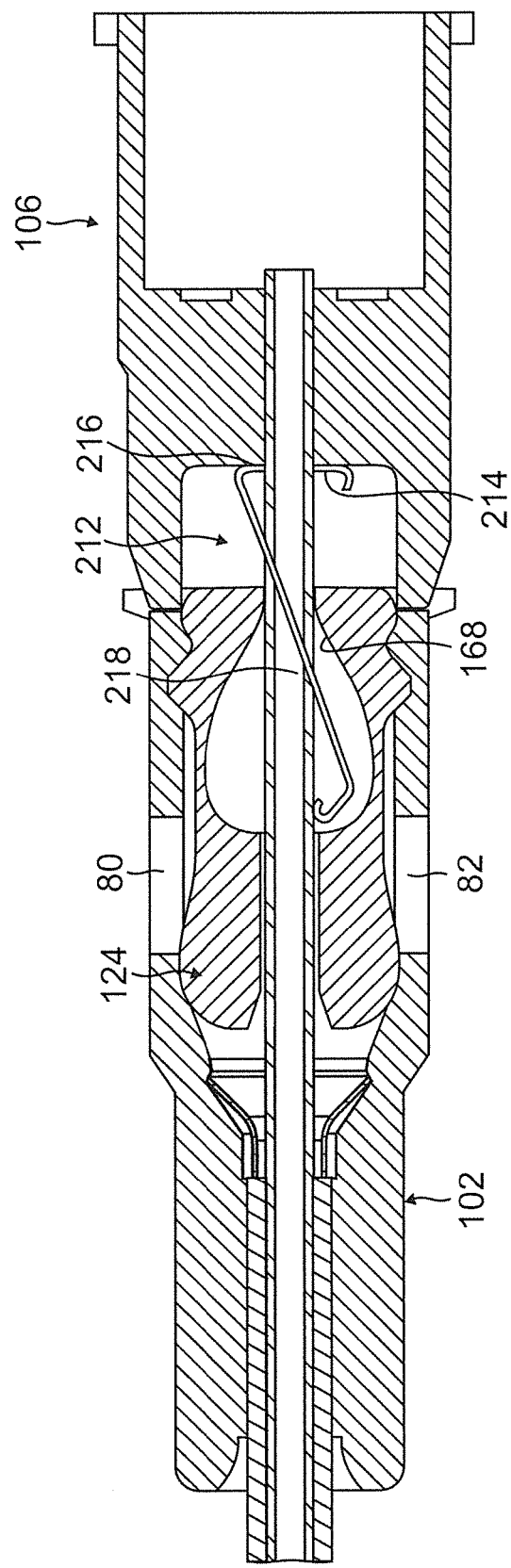
FIG. 9 is a schematic cross-sectional side view of an alternative catheter assembly with a valve and an alternative tip protector.

With reference now to FIG. 9, an alternative safety IVC 210 is shown, which is similar to the safety IVC 100 of FIG. 1 with the exception of the needle guard 212. In the present embodiment, the needle guard has a single guard arm that crosses the needle axis at the location of the slit 168. Thus, the needle guard 212, like the guard 156 of FIG. 1, has a section that is located internally of the valve and a section that is located externally of the valve. The needle guard further includes a proximal wall 214 having an opening 216 positioned around or over the needle. The proximal wall 214 and the opening 216 may be configured to engage a change in profile on the needle to stop the distal advancement of the needle guard off of the needle, the proximal wall may instead cant over from its more vertical position shown so that the opening 216 grips the needle to stop the distal advancement, or the arm 218, which has an opening for the needle to pass therethrough, can further cant to grip the needle without a change in profile. Or both openings together cooperate to cant and grip the needle. In still other examples, a tether (not shown) may be used to hold the needle guard 212 to the needle hub 106. In one example, the needle guard 212 is one of the guards shown in U.S. Pat. No. 6,616,630.

Figure 10:
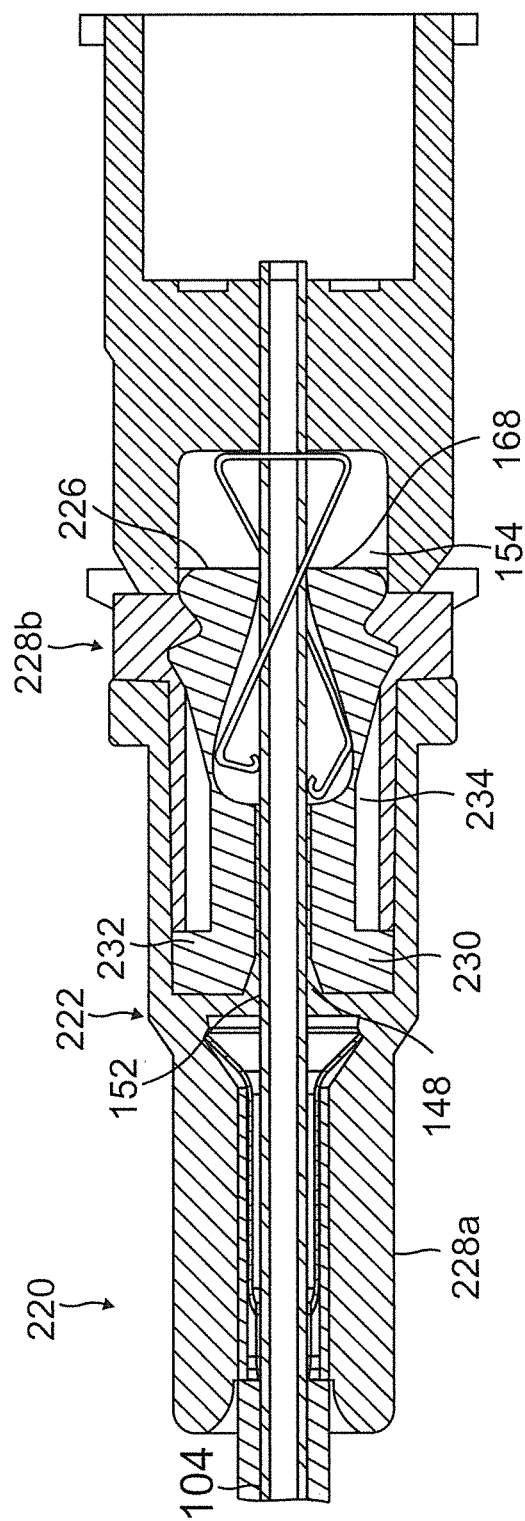
FIG. 10 is a schematic cross-sectional side view of yet another alternative catheter assembly with a valve provided in accordance with aspects of the present disclosure.

FIG. 10 is a cross-sectional side view of an alternative safety IVC 220 provided in accordance with aspects of the present disclosure. The safety IVC comprises a catheter hub 222 comprising a catheter tube 104 and an elastic valve 226, similar to the safety IVCs of FIGS. 1 and 9. In the present embodiment, the catheter hub 222 is formed from multiple components. In particular, the catheter hub 222 comprises a distal hub section 228a and a proximal hub section 228b having a gap or channel 230 formed therebetween for compressing a distal flange 232 on the elastic valve 226, which differs from the enlarged distal portion 142 incorporated with the valve of FIG. 3. The elastic valve 226 further comprises a distal recess 148, a through bore 152, and an enlarged interior bore section 154 for receiving part of a needle guard (not shown), which has a portion located inside the enlarged interior bore section 154 and a portion extending proximally and out of the elastic valve. A gap 234 is provided between the elastic valve 226 and the catheter hub 222 to provide space for the valve body to expand when enlarged by a male implement, such as that shown in connection with FIG. 8.

Figure 11:
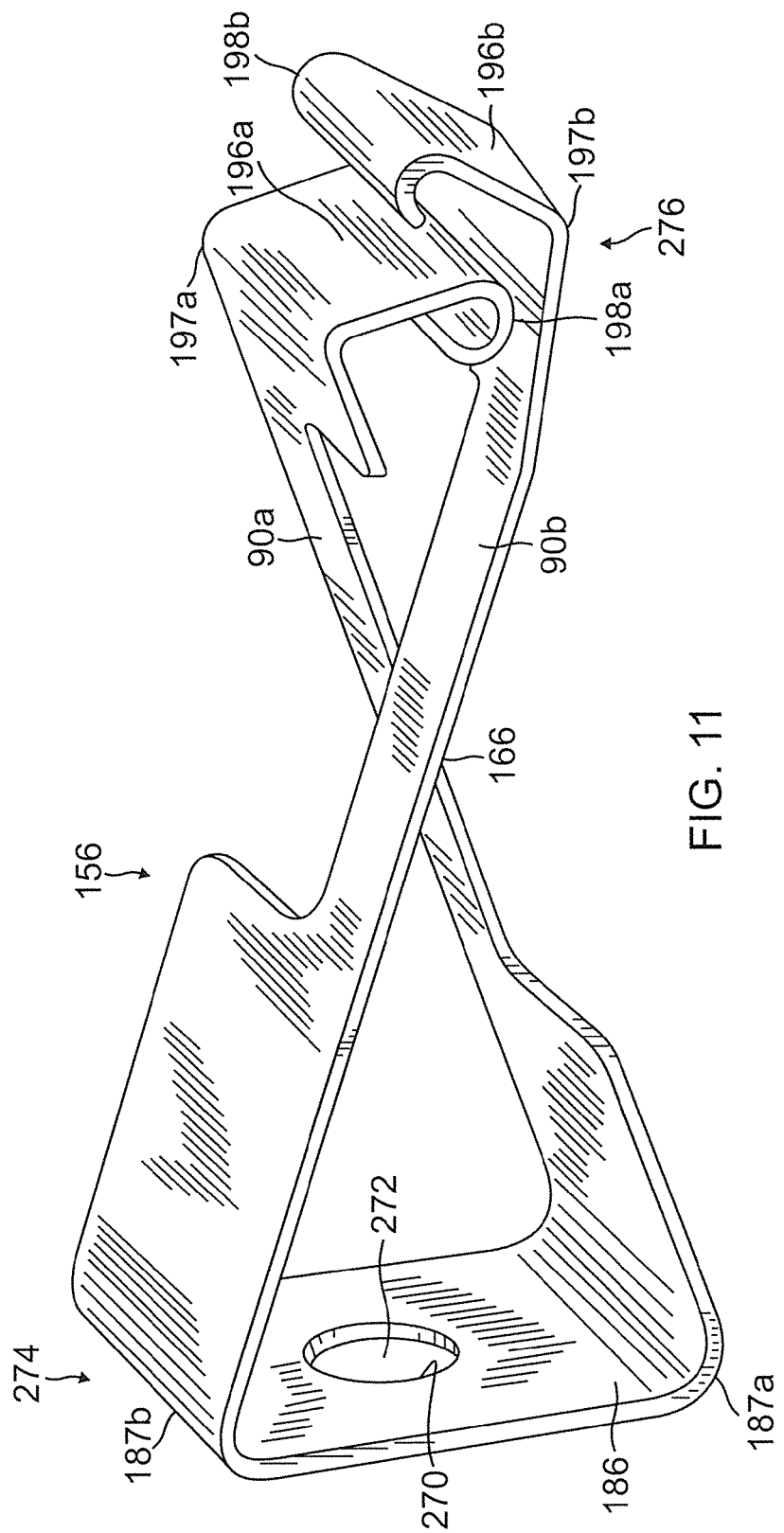
FIG. 11 is an isometric view of the tip protector shown in the catheter assemblies of FIGS. 1 and 4.

FIG. 11 is a perspective view of the needle guard or tip protector 156 of FIG. 1. As shown, the guard comprises a proximal wall 186 comprising a perimeter 270 defining an opening 272. The proximal wall 186 is located on the proximal end 274 of the guard, which is exposed or external of the elastic valve when in the ready to use position, as shown in FIG. 1. The guard 156 is further shown with a reduced section 166 and a distal portion 276 having the two distal walls 196a, 196b. In use, the two distal walls are located internally of the valve, in the enlarged interior space.

There are bends or curved portions 187a and 187b between the proximal wall 186 and arms 90a and 90b respectively. Likewise there are bends or curved portions 197a and 197b between arms 90a and 90b and distal walls 196a and 196b respectively. The distance between the bends or curved portions 187a and 187b should be the same or smaller than the distance between the bends or curved portions 197a and 197b, when a needle is in between the distal walls 196a and 196b. This is to facilitate the assembly and allow for easy removal of the assembly tools shown in FIGS. 5, 5A, 5B, 5C and 5D.

At the end of the distal walls 196a and 196b opposite the bends or curved portions 197a and 197b are lips or hooks 198a and 198b, respectively. In one example, the distance between the inside edge of lips or hooks 198a and 198b and the arms 90a and 90b, respectively, should be about half the diameter of the needle to facilitate blocking the needle tip from escaping the tip protector distally. In other examples, the dimension is slightly more than half or slightly less than half the diameter of the needle.

FIG. 12 is a perspective view of the needle guard 212 of FIG. 9. As shown, the guard has an arm 218 comprising an elongated opening 290, which in one embodiment is an elongated slit having round ends 300a, 300b, and a distal wall 292 having a distal curved lip or hook 294. The arm further has a ramped section 296 along a proximal direction. A proximal wall 214 is provided with an opening 216 and a proximal curved lip or foot 298 at the proximal end of the needle guard 212. In the ready position, the needle projects through the proximal opening 216 and the elongated opening 290 and over the top of the distal curved lip 294. In the activated position, the needle is retracted proximally until the needle tip moves proximal of the distal curved lip 294. At that point, the arm 218, which is no longer biased by the needle, swings radially so that the two rounded ends 300a, 300a of the elongated opening 216 can grip the needle to limit or restrict the needle guard from moving distally off of the needle tip. The distance between the inside edge of lip or hook 294 and arm 218 of needle guard 212 should be about one needle diameter to facilitate blocking the tip of the needle from escaping the tip protector distally.

FIG. 13 is a perspective view of another alternative needle guard device 213 in accordance with further aspects of the present disclosure. The alternative needle guard 213 has a distal wall 292 turned around 180 degrees to point downwards compared to the guard in FIG. 12. Thus, the guard is understood to comprise a distal wall and a proximal wall that both point in the same direction. In this alternative needle guard, the elongated opening 290 is optional and could be eliminated. The arm 218a could be much narrower or even curved radially compared to the arm of FIG. 12 to more closely match the shape of the needle and thus reduce the material protruding through the proximal slit of the elastic valve 126 to a minimum. In one example, the width of the arm 218a is approximately the diameter of the needle plus two times the thickness of the arm. In other examples, the width can be greater or less. The height of the curve of the arm can be approximately half the needle diameter or less. If the height of the arm 218a was less than half the diameter of the needle, then the width could be less than the needle diameter. Having arm 218a curved in a cross section perpendicular to the needle increases its spring strength. The more the curve, the stiffer is the arm.

Although limited embodiments of safety IVCs and their components have been specifically described and illustrated herein, many modifications and variations will be apparent to those skilled in the art. For example, the various needle guards disclosed may incorporate other features, such as additional guard surfaces to cover the circumference of the needle tip, etc. Furthermore, it is understood and contemplated that features specifically discussed for one safety IVC embodiment may be adopted for inclusion with another safety IVC embodiment, provided the functions are compatible. For example, while a needle guard is not shown in connection with FIG. 10, any of the needle guards discussed elsewhere herein may be used with the catheter hub of FIG. 10 using one of the installation tools disclosed herein. Another example includes using additional guard structures, such as a third hub for housing part of the guard that extends outside the elastic valve. Accordingly, it is to be understood that the safety IVCs and their components constructed according to principles of the disclosed device, system, and method may be embodied other than as specifically described herein. The disclosure is also defined in the following claims.

The invention claimed is:

1. A safety IV catheter comprising:
a catheter hub attached to a catheter tube comprising an interior hub cavity, said catheter hub comprising an end opening defining a plane;
a valve attached to the catheter hub, said valve comprising an interior cavity, a proximal end wall exposed externally of the catheter hub and accessible for wiping at the plane, and a slit formed through the proximal end wall to access the interior cavity, said valve being configured to stop or restrict the flow of blood when the valve is closed;
a needle hub attached to a needle and the needle extending through the catheter tube;

a tip protector comprising a distal end portion, a proximal wall comprising an opening, and a small profile located between the distal end portion and the proximal wall; and wherein the distal end portion of the tip protector is located inside the interior cavity of the valve and the proximal wall is located externally of the valve and proximal of the plane.

2. The safety IV catheter of claim 1, wherein the needle comprises a crimp.

3. The safety IV catheter of claim 2, wherein the crimp is sized larger than the opening on the proximal wall.

4. The safety IV catheter of claim 1, wherein the small profile is located at the slit.

5. The safety IV catheter of claim 1, wherein the tip protector comprises two arms that cross one another and wherein the small profile is located where the two arms cross.

6. The safety IV catheter of claim 1, wherein the valve extends proximally of the catheter hub and has at least a portion that is wider than the catheter hub.

7. The safety IV catheter of claim 1, further comprising an installation tool for mounting the distal portion of the tip protector through the slit.

8. A safety IV catheter comprising:
a catheter hub attached to a catheter tube, said catheter hub comprising an interior hub cavity and an end opening defining a plane;
a valve attached to the catheter hub, said valve comprising an interior cavity, a proximal end wall located at a proximal end of the catheter hub, and a slit on the valve that is deflectable to an open position to permit fluid flow through the interior cavity and to a closed position to stop or restrict fluid flow through the valve, said valve being configured to stop or restrict the flow of blood when the valve is closed;
a needle hub attached to a needle and the needle extending through the catheter tube;
a tip protector comprising a distal end portion of a first dimension, a proximal wall of a second dimension comprising an opening having an opening dimension, and a center section of a third dimension located between the distal end portion and the proximal wall, the first dimension being larger than the second and the third dimensions and the third dimension is smaller than both the first and the second dimension; and
wherein the distal end portion of the tip protector is located inside the interior cavity of the valve and the proximal wall is located externally of the valve and proximal of the plane.

9. The safety IV catheter of claim 8, wherein the needle comprises a crimp.

10. The safety IV catheter of claim 9, wherein the crimp is sized larger than the opening on the proximal wall.

11. The safety IV catheter of claim 8, wherein the center section of the tip protector is located at the slit.

12. The safety IV catheter of claim 8, wherein the tip protector comprises two arms that cross one another and wherein the center section is located where the two arms cross.

13. A safety IV catheter comprising:
a catheter hub attached to a catheter tube, the catheter hub having an interior hub cavity; a valve located inside the interior hub cavity of the catheter hub, said valve comprising an interior cavity and a proximal valve surface comprising a slit, said valve being configured to stop or restrict the flow of blood when the valve is closed;
a needle hub attached to a needle and the needle extending through the catheter tube;
a tip protector comprising a distal end portion, a proximal wall comprising an opening, and a small profile located between the distal end portion and the proximal wall; and
wherein the distal end portion of the tip protector is located inside the interior cavity of the valve, the small profile is located at the slit, and the proximal wall is located externally of the valve and proximal of the proximal valve surface.

14. The safety IV catheter of claim 13, wherein an elastomeric body of the valve defines the interior cavity.

15. The safety IV catheter of claim 13, wherein the catheter hub comprises an open proximal end defining a plane and wherein the proximal valve surface is located at the plane of the open proximal end.

16. The safety IV catheter of claim 13, wherein the proximal wall of the tip protector is located proximally an open proximal end of the catheter hub.

17. The safety IV catheter of claim 13, wherein the proximal valve surface is located at an open proximal end of the catheter hub for wiping.

18. A method for manufacturing a safety IV catheter comprising:
forming a catheter hub and attaching the catheter hub to a catheter tube,
attaching a valve to the catheter hub, said valve comprising an interior cavity, a proximal end wall, and a slit formed at the proximal end wall, said valve being configured to stop or restrict the flow of blood when the valve is closed;
forming needle hub and attaching the needle hub to a needle and the needle extending through the catheter tube;
placing a tip protector, at least in part, inside the interior cavity of the valve, said tip protector comprising a distal end portion, a proximal wall comprising an opening, and a small profile located between the distal end portion and the proximal wall so that the small profile is located at the slit.

19. The method of claim 18, further comprising placing a tool comprising a slit around the needle before placing the tip protector inside the interior cavity of the valve.

20. The method of claim 19, further comprising placing a distal end of the tool in through the slit before placing the tip protector inside the interior cavity of the valve.

21. The method of claim 19, further comprising pushing the distal end portion of the tip protector through a bore of the tool.

22. The method of claim 18, further comprising removing the needle from the catheter hub and the needle hub.

23. The method of claim 22, further wiping the proximal end wall of the valve with an antiseptic solution.

24. The method of claim 18, wherein the needle comprises a crimp for engaging the opening on the proximal wall of the tip protector.

25. The method of claim 18, wherein the tip protector has a single arm passing through the slit at the proximal end wall of the valve.

26. The method of claim 18, wherein the tip protector comprises two arms that cross one another and wherein the small profile is located where the two arms cross.

27. The method of claim 18, wherein the needle hub comprises a Luer taper.

28. The method of claim 18, where the slit comprises at least three slit sections forming at least two movable slabs.

* * * * *

UNITED STATES PATENT AND TRADEMARK OFFICE
CERTIFICATE OF CORRECTION

PATENT NO.       : 9,623,210 B2
APPLICATION NO.  : 13/951168
DATED            : April 18, 2017
INVENTOR(S)      : Kevin Woehr Page 1 of 1

It is certified that error appears in the above-identified patent and that said Letters Patent is hereby corrected as shown below:

In the Specification

In Column 7, Line 23, delete "sulfa diazine," and insert -- sulfadiazine, --, therefor.

Signed and Sealed this
Twenty-sixth Day of September, 2017

Joseph Matal
*Performing the Functions and Duties of the*
*Under Secretary of Commerce for Intellectual Property and*
*Director of the United States Patent and Trademark Office*